United States Patent [19]

Ninomiya et al.

[11] Patent Number: 5,266,598

[45] Date of Patent: Nov. 30, 1993

[54] SKIN DISINFECTANT COMPOSITIONS

[75] Inventors: Noboru Ninomiya, Amagasaki; Takahiro Mizuno, Osaka; Takashi Tamura, Takatsuki; Nobukatsu Sato, Nara, all of Japan

[73] Assignee: Maruishi Pharmaceutical Co., Ltd., Osaka, Japan

[21] Appl. No.: 927,989

[22] Filed: Aug. 11, 1992

[30] Foreign Application Priority Data

Jun. 15, 1990 [JP] Japan .................................. 158044

[51] Int. Cl.$^5$ ............................................. A61K 31/155
[52] U.S. Cl. ................................................... 514/635
[58] Field of Search ........................................ 514/635

[56] References Cited

U.S. PATENT DOCUMENTS 4,062,976 12/1977 Michaels ........................ 514/644 X
5,030,659 7/1991 Bansemir et al. .................. 514/635

FOREIGN PATENT DOCUMENTS 1338003 11/1973 United Kingdom .

OTHER PUBLICATIONS

1973 Edition of British Pharmacopoeia pp. 3, 273 and 274.

Primary Examiner—Leonard Schenkman
Attorney, Agent, or Firm—Millen, White, Zelano & Branigan

[57] ABSTRACT

Presented are compositions for disinfection of the skin. The composition is characterized in that it contains in an aqueous medium; 0.5 to 10 w/v % of chlorhexidine digluconate, 5 to 25 w/v % of polyoxyethylene alkyl ether, 1 to 5 w/v % of fatty acid diethanolamide, 1 to 5 w/v % of alkyldimethylamine oxide, and macrogol at less than 10 w/v %. The polyoxyethylene alkyl ether and macrogol may be replaced with 10 to 35 w/v % of polyoxyethylene alkylphenyl ether. The composition may further contain 5 w/v % or lower polyoxyethylene lanolin.

Since the composition will not solidify even when its solvent is evaporated, the plugging of the outlet opening of the dispenser will be avoided.

6 Claims, No Drawings

SKIN DISINFECTANT COMPOSITIONS

BACKGROUND OF THE INVENTION

The present invention relates to disinfecting compositions which is used to clean and disinfect the hands and fingers of medical personnels such as medical doctors and nurses.

For the disinfection of the hands and fingers of the medical personnel, for example before and after a surgical operation, liquid compositions which contain chlorhexidine salt, such as gluconate, and surfactants are used as disinfectants. Such compositions have to meet the criteria including:
the chlorhexidine contained in the composition will remain stable for a long period of time,
they possess satisfactory detergency,
they have proper lather producing activity,
they allow easy rinsing, and
they do not have any skin irritating properties.

Therefore, the proper selection of surfactants which will be used concomitantly with chlorhexidine salts is important, and preference is given for non-ionic surfactants.

Japanese patent publication No. 38046/77 and Japanese laid open patent application No.104003/89 disclose a disinfecting composition which contains a chlorhexidine salt and, as a surfactant, a block copolymer of ethylene oxide and propylene oxide, which is known as "pluronic". However, compositions containing pluronic as a primary surfactant has been found to carry a disadvantage, i.e., they may tightly solidify and plug the outlet opening of a dispenser through the evaporation of the medium such as water and ethanol. The object of the present invention, therefore, is to provide a chlorhexidine containing skin disinfecting composition which is free of such a disadvantage.

SUMMARY OF THE INVENTION

The present invention provides a skin disinfecting composition which includes, in an aqueous medium, the following ingredients.

| chlorhexidine digluconate | 0.5-10 w/v % |
|---|---|
| polyoxyethylene alkyl ether | 5-25 w/v % |
| fatty acid diethanolamide | 1-5 w/v % |
| alkyldimethylamine oxide | 1-5 w/v % |
| macrogol | less than 10 w/v % |

The present invention also provides a skin disinfecting composition which includes, in an aqueous medium, the following ingredients;

| chlorhexidine digluconate | 0.5-10 w/v % |
|---|---|
| polyoxyethylene alkylphenyl ether | 10-35 w/v % |
| fatty acid diethanolamide | 1-5 w/v % |
| alkyldimethylamine oxide | 1-5 w/v % |

Either of the aforementioned compositions may contain 5 w/v % or less of polyoxyethylene lanolin. They may also contain conventional ingredients, such as pH adjusting agents and coloring agents, when they are necessary.

In using the composition of the present invention, hands, fingers and the arms below the elbow are first wetted with water, and then an appropriate amount of the composition, for example 2-5 ml, is put onto a palm and applied to the washed areas, and after adequate washing, it is rinsed away with running water. The procedure may be repeated, when necessary.

The composition according to the present invention meets all of the aforementioned requirements that are requisite for disinfecting compositions of this type. Moreover, it will not tightly solidify even when its medium, water or ethanol, is evaporated, and thus will not plug the outlet opening of a dispenser.

DETAILED DISCUSSION

The present invention is characterized in that polyoxyethylene alkyl ether or polyoxyethylene alkylphenyl ether is incorporated as a primary surfactant. Both of these are non-ionic and chemically stable, and both possess satisfactory detergency. Moreover, what is important in the present invention is that, unlike pluronic, they will not tightly solidify to plug the outlet opening of a dispenser, even when the medium have been evaporated.

Polyoxyethylene alkyl ether can be obtained by conducting an addition reaction of long-chain fatty alcohols with about 5-100 mole of ethylene oxide. The fatty alcohol moiety is generally of 8-20 carbon atoms, for example octyl, nonyl, oleyl, lauryl, myristyl, cetyl, stearyl and the like. The term "alkyl" as used herein includes alkenyl groups such as oleyl group.

In the case where polyoxyethylene alkyl ether is used, it is necessary to concurrently use a macrogol (with average molecular weight of 10,000-50,000) as a thickener. If other macromolecular thickeners are used, disadvantages will result, such as lowering of the disinfecting activity and imcomplete dissolving or mixing. In addition, the composition incorporating macrogol is easier to rinse away.

Instead of concurrently using polyoxyethylene alkyl ether and macrogol (polyethylene glycol; PEG), polyoxyethylene alkylphenyl ether may be used independently. This can be obtained by conducting an addition reaction of alkylphenols, such as nonylphenol, with 5-20 mole of ethylene oxide.

Alkyldimethylamine oxide is concurrently used with the aforementioned surfactants in order to give the composition an adequate lather producing property. The "alkyl-" used in the aforementioned two ingredients denotes long-chain aliphatic hydrocarbon groups such as oleyl group, likewise.

Fatty acid diethanolamide is incorporated to improve the quality of the foam, in particular to give the form a creamy touch similar to solid bath soap. It also has an effect to improve the durability of the foam.

As an optional ingredient, polyoxyethylene lanolin may be incorporated in an amount of 5 w/v % or lower, for example 1 w/v %. This is effective to properly regulate the lather producing property, quality of the foam, durability of the foam and the like. The aforementioned ingredients are dissolved in an aqueous medium. Although the medium usually, is water, it may contain 10 w/v % or lower of lower alcohols such as ethanol, isopropanol, preferably ethanol. The addition of ethanol will enhance the stability of the composition.

The composition may contain a minute amount of coloring agent (red, for example) to indicate that it is a disinfectant for external use, and a pH adjusting agent such as gluconic acid to achieve pH 5.5-7.0.

Although the examples of the present invention will be set forth below, it will become apparent to anyone skilled in the art that the present invention is not limited by them and that various alterations and modifications may be made within the scope of the appended claims.

EXAMPLE 1

| Ingredients | Incorporated amount (in 100 ml composition) |
|---|---|
| chlorhexidine digluconate (20 w/v soln.) | 20 ml |
| macrogol 20000 | 7 g |
| lauromacrogol | 5 g |
| polyoxyethylene oleyl ether (30 E.O.) | 5 g |
| polyoxyethylene cetyl ether (40 E.O.) | 5 g |
| lauric acid diethanolamide | 2 g |
| polyoxyethylene lanolin (17 E.O.) | 1 g |
| dimethyllaurylamine oxide | 3.5 g |
| red pigment (35% solution) | minute amount |
| gluconic acid | 1 g |
| ethanol | 5.5 g |
| purified water | q.s. |

EXAMPLE 2

| Ingredients | Incorporated amount (in 100 ml composition) |
|---|---|
| chlorhexidine digluconate solution (20 w/v %) | 20 ml |
| polyoxyethylene nonylphenyl ether (9 E.O.) | 22.0 g |
| lauric acid diethanolamide | 3.0 g |
| dimethyllaurylamine oxide | 3.5 g |
| polyoxyethylene lanolin (17 E.O.) | 1.0 g |
| red pigment | minute amount |
| gluconic acid | 1.0 g |
| ethanol | 5.5 g |
| purified water | q.s. |

EXAMPLE 3

The minimum inhibitory concentration test and the minimum bactericidal concentration test were carried out as follows using the composition described in EXAMPLE 1.

1. Test methods
   (1) Minimum Inhibitory Concentration (MIC) Test
   Culture Medium
   Inoculating Medium
   For bacteria: sensitivity bouillon (EIKEN)
   For fungi (yeast): Glucose peptone broth (NIPPON SEIYAKU)
   2) Medium for Sensitivity Assay
   For bacteria: medium for sensitivity disc (EIKEN)
   For fungi (yeast): Glucose peptone agar (NIPPON SEIYAKU)
   (b) Preparation of the Suspensions of Micro-Organisms for Inoculation
   Fresh suspensions of the micro-organisms which were prepared by inoculation from the storage medium to a 10 ml of the inoculating medium, followed by three consecutive subcultures at 37° C. for 24 hours for each generation. Only Ps. aeruginosa was filtered through a Whatman No. 4 filter paper to remove the membrane developed.
   (c) Method for the Measurement
   An aqueous solution containing chlorhexidine digluconate at 0.5 w/v % prepared by the addition of sterilized water to the composition described in EXAMPLE 1 was used as a bulk solution. To 1 ml of each solution obtained from a sequential twofold dilution of the bulk solution with sterilized water was added 9 ml of the medium for sensitivity assay that had been warmed at about 50° C. After the mixture was made homogeneous, it was made into a plate.

This plate medium for sensitivity assay was inoculated with about 2 cm streak of a test micro-organism in one platinum loop using a 1 μl inoculation loop (Nunc). After inoculation, the medium was cultured for 24 hours at 37° C., and the growth of the micro-organisms was observed.

The minimal concentration at which the growth was completely inhibited was regarded as the minimum inhibitory concentration (MIC) of the tested agent against the tested micro-organism. If only a few (not more than 5) colonies were observed, they were regarded as variants and the growth was regarded as being inhibited.

(2) The Minimum Bactericidal Concentration (MBC) Test
   (a) Culture Medium
      1) Inoculating Medium For bacteria: sensitivity bouillon (EIKEN) For fungi (yeast): Glucose peptone broth (NIPPON SEIYAKU)
      2) Medium for Sensitivity Assay and Medium for Secondary Culture
      For bacteria: sensitivity bouillon (EIKEN)
      For fungi (yeast): Glucose peptone broth (NIPPON SEIYAKU)
   (b) Preparation of the Suspensions of Micro-Organisms for Inoculation
      A fresh suspension of the micro-organisms prepared by being transferred from the storage medium to the inoculating medium and subjected to a culture at 37° C. for 24 hours was diluted to make $1 \times 10^6$ cells/ml. Only Ps. aeruginosa was first filtered through Whatman No. 4 filter paper to remove membrane developed, and then diluted.
   (c) Method for the measurement
      An aqueous solution containing chlorhexidine digluconate at 0.5 w/v % prepared by the addition of sterilized water to the composition described in EXAMPLE 1 was used as a bulk solution, and the solution was subjected to a sequential twofold dilution using the liquid medium for sensitivity assay. Then, 1 ml each of the liquid media containing the agent at different concentrations was inoculated with a 0.05 ml of the suspension of the micro-organism for inoculation, and cultured for 24 hours at 37° C., then observed for a growth of the micro-organisms on the basis of clouding of the medium. As for the tested samples which were not observed to grow, 0.05 ml of each was further inoculated to a 1 ml a medium for sensitivity assay that did not include the agent, and cultured again for 24 hours at 37° C. and observed for a growth of the micro-organisms.

The lowest concentration at which any growth of the micro-organisms was not observed was regarded as the minimum bactericidal concentration.

2. Frequency of the Test

Both tests were carried out 5 times for each microorganism.

3. Test Results

MIC is shown in Table 1, and MBC in Table 2.

TABLE 1

MIC value

| Micro-organism | | No. | MIC (μg/ml) Ex. 1 composition |
|---|---|---|---|
| (1) | Staphylococcus aureus IFO 13276 | 1 | 1.0 |
| | | 2 | 1.0 |
| | | 3 | 2.0 |
| | | 4 | 2.0 |
| | | 5 | 2.0 |
| (2) | Escherichia coli NIHJC | 1 | 2.0 |
| | | 2 | 2.0 |
| | | 3 | 2.0 |
| | | 4 | 2.0 |
| | | 5 | 2.0 |
| (3) | Pseudomonas aeruginosa IFO 13275 | 1 | 125 |
| | | 2 | 125 |
| | | 3 | 125 |
| | | 4 | 125 |
| | | 5 | 125 |
| (4) | Serratia marcescens IFO 12648 | 1 | 250 |
| | | 2 | 250 |
| | | 3 | 125 |
| | | 4 | 125 |
| | | 5 | 250 |
| (5) | Candida albicans IFO 1061 | 1 | 62.5 |
| | | 2 | 62.5 |
| | | 3 | 62.5 |
| | | 4 | 62.5 |
| | | 5 | 62.5 |

TABLE 2

MBC value

| Micro-organism | | No. | MBC (μg/ml) Ex. 1 composition |
|---|---|---|---|
| (1) | Staphylococcus aureus IFO 13276 | 1 | 2.4 |
| | | 2 | 2.4 |
| | | 3 | 2.4 |
| | | 4 | 4.9 |
| | | 5 | 2.4 |
| (2) | Escherichia coli NIHJC | 1 | 2.4 |
| | | 2 | 2.4 |
| | | 3 | 1.2 |
| | | 4 | 1.2 |
| | | 5 | 1.2 |
| (3) | Pseudomonas aeruginosa IFO 13275 | 1 | 4.9 |
| | | 2 | 10.0 |
| | | 3 | 4.9 |
| | | 4 | 4.9 |
| | | 5 | 4.9 |
| (4) | Serratia marcescens IFO 12648 | 1 | 20 |
| | | 2 | 20 |
| | | 3 | 20 |
| | | 4 | 39 |
| | | 5 | 20 |
| (5) | Candida albicans IFO 1061 | 1 | 39 |
| | | 2 | 39 |
| | | 3 | 39 |
| | | 4 | 39 |
| | | 5 | 39 |

What is claimed is:

1. A composition for disinfection of the skin comprising, in an aqueous medium;

0.5 to 10 w/v % of chlorhexidine digluconate, 5 to 25 w/v % of a polyoxyethylene alkyl ether, 1 to 5 w/v % of a fatty acid diethanolamide, 1 to 5 w/v % of an alkyldimethylamine oxide, and a macrogol thickener of a molecular weight of 10,000–50,000 at less than 10 w/v %.

2. The composition for disinfection of the skin according to claim 1, which further contains a lower polyoxyethylene lanolin in an amount of up to 5 w/v %.

3. A composition for disinfection of the skin comprising, in an aqueous medium;

0.5 to 10 w/v % of chlorhexidine digluconate, 10 to 35 w/v % of a polyoxyethylene alkylphenyl ether, 1 to 5 w/v % of a fatty acid diethanolamide, and 1 to 5 w/v % of a alkyldimethylamine oxide.

4. The composition for disinfection of the skin according to claim 3, which further contains a lower polyoxyethylene lanolin in an amount of up to 5 w/v %.

5. A composition according to claim 1, adapted for dispensing without clogging from a dispenser, wherein the alkyl group of the polyoxyethylene alkyl ether is of 8–20 carbon atoms.

6. A composition according to claim 3, adapted for dispensing without clogging from a dispenser, wherein the alkyl group of the polyoxyethylene alkyl ether is of 8–20 carbon atoms.

* * * * *